United States Patent
Narula et al.

(10) Patent No.: US 7,491,688 B2
(45) Date of Patent: *Feb. 17, 2009

(54) CYCLOPROPANECARBOXALDEHYDES AND THEIR USE IN PERFUME COMPOSITIONS

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/837,766

(22) Filed: Aug. 13, 2007

(65) Prior Publication Data

US 2008/0026979 A1  Jan. 31, 2008

Related U.S. Application Data

(62) Division of application No. 11/424,941, filed on Jun. 19, 2006, now Pat. No. 7,271,294, which is a division of application No. 11/154,400, filed on Jun. 16, 2005, now Pat. No. 7,087,796.

(51) Int. Cl.
*A61K 7/46* (2006.01)
*C07C 47/105* (2006.01)

(52) U.S. Cl. ......................................... 512/27; 568/445

(58) Field of Classification Search ............... 512/27; 568/445

See application file for complete search history.

(56) References Cited

U.S. PATENT DOCUMENTS

| 4,759,880 A * | 7/1988 | Nicolaou et al. ............. 554/221 |
| 7,087,796 B1 * | 8/2006 | Narula et al. ................ 568/445 |
| 7,271,294 B2 * | 9/2007 | Narula et al. ................ 568/445 |

* cited by examiner

*Primary Examiner*—Sikarl A Witherspoon
(74) *Attorney, Agent, or Firm*—Elizabeth M. Quirk; XuFan Tseng; Joseph F. Leightner

(57) ABSTRACT

The present invention is directed to novel cyclopropanecarboxaldehyde compounds of the general formula

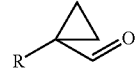

wherein R is a straight, branched, or cyclic hydrocarbon moiety consisting of 6 to 30 carbon atoms and containing single and/or double bonds.

17 Claims, No Drawings

CYCLOPROPANECARBOXALDEHYDES AND THEIR USE IN PERFUME COMPOSITIONS

RELATED APPLICATIONS

This application is a divisional application of the U.S. patent application Ser. No. 11/424,941, filed Jun. 19, 2006, and now U.S. Pat. No. 7,271,294, which is a divisional application of U.S. patent application Ser. No. 11/154,400, filed Jun. 16, 2005, now U.S. Pat. No. 7,087,796 now U.S. patent application Ser. No. 90/010,120, which is under re-examination, each of which is hereby incorporated by reference in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel cyclopropanecarboxaldehyde compounds, represented by the general structure of Formula I set forth below:

Formula I wherein R is a straight, branched, or cyclic hydrocarbon moiety consisting of 1 to 20 carbon atoms and containing single and/or double bonds.

Another embodiment of the invention is a method for enhancing a perfume composition by incorporating an olfactory acceptable amount of the compounds provided above.

Another embodiment of the invention is a method for enhancing a perfume composition by incorporating an olfactory acceptable amount of the compounds below:

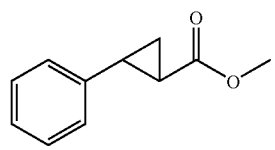

Formula II

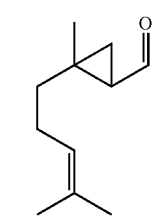

Formula III

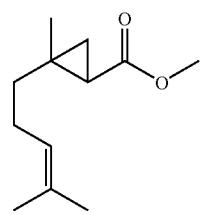

Formula IV

These and other embodiments of the present invention will be apparent by reading the following specification.

DETAILED DESCRIPTION OF THE INVENTION

In Formula I above, R represents straight, branched, or cyclic hydrocarbon moiety consisting of 1 to 20 carbon atoms and containing single and/or double bonds. Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable cyclic hydrocarbon moieties include cyclopropane, cyclobutane, cyclopentane, cyclopentene, 1,4-cyclopentene, cyclohexane, cyclohexene and the like. Suitable hydrocarbon moieties containing double bonds include ethene, propene, 1-butene, 2-butene, penta-1-3-deine, hepta-1,3,5-triene and the like.

In the preferred embodiment of the invention, the novel compounds of the present invention are represented by the following structures:

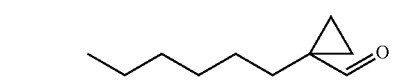

Formula V

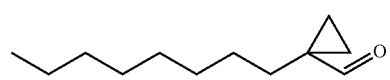

Formula VI

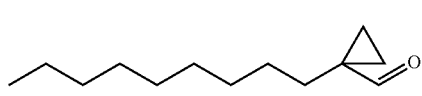

Formula VII

-continued

Formula VIII

Formula IX

Formula X

Formula XI

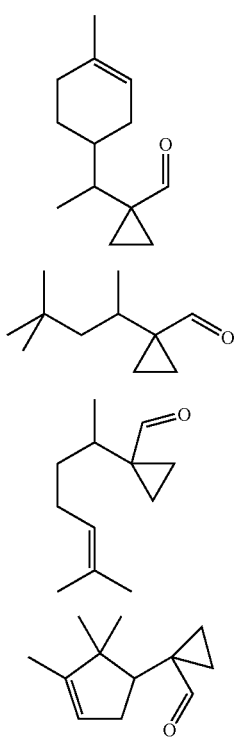

Those with the skill in the art will appreciate that the compound of Formula V is 1-hexyl-cyclopropanecarboxaldehyde, the compound of Formula VI is 1-octyl-cyclopropanecarboxaldehyde, the compound of Formula VII is 1-nonyl-cyclopropanecarboxaldehyde, the compound of Formula VIII is 1-[1-(4-methyl-3-cyclohexen-1-yl)-ethyl]-cyclopropanecarboxaldehyde, the compound of Formula IX is 1-(1,3,3-trimethylbutyl)-cyclopropanecarboxaldehyde, the compound of Formula X is 1-(1,5-dimethyl-4-hexenyl)-cyclopropanecarboxaldehyde and the compound of Formula XI is 1-(2,2,3-trimethyl-3-cyclopenten-1-yl)-cyclopropanecarboxaldehyde.

The table below lists additional compounds derived from Formula I that are described in the present invention:

| R | Compound |
|---|---|
| $(CH_2)_2CH_3$ | 1-propyl-cyclopropanecarboxaldehyde |
| $(CH_2)_4CH_3$ | 1-pentyl-cyclopropanecarboxaldehyde |
| $CHCH(CH_2)_3CH_3$ | 1-hex-1-enyl-cyclopropanecarboxaldehyde |
| $C(CH_3)_3$ | 1-tert-butyl-cyclopropanecarboxaldehyde |
| $(CH_2)_3C(CH_3)_3$ | 1-(4,4-dimethyl-pentyl)-cyclopropanecarboxaldehyde |
| $(CH)_4CH_2CH_3$ | 1-hex-1-dienyl-cyclopropanecarboxaldehyde |
| $CH_2C(C_3H_7)(C_4H_9)H$ | 1-(2-propyl-hexyl)-cyclopropanecarboxaldehyde |
| $C(CH_3)(CHC(CH_3)_3)$ | 1-(1,3,3-trimethyl-but-1-enyl)-cyclopropanecarboxaldehyde |
| $C_6H_{11}$ | 1-cyclohexyl-cyclopropanecarboxaldehyde |
| $C_6H_9$ | 1-cyclohex-3-enyl-cyclopropanecarboxaldehyde |

The compounds of the present invention may be prepared from the corresponding alkenes, via Corey's cyclopropanation reaction. As described in the Examples below, compounds of Formulae V-XI may be prepared via Corey's cyclopropanation reaction from the corresponding alkenes of the compounds below:

Formula XII

Formula XIII

Formula XIV

Formula XV

Formula XVI

Formula XVII

Formula XVIII

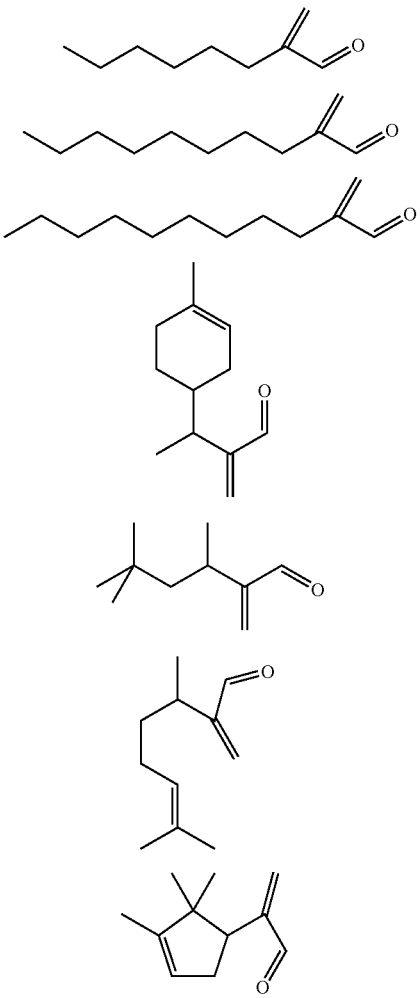

The alkenes of Formulae XII-XVIII are fragrance products commercially available from International Flavors & Fragrances Inc., New York, N.Y. The compound of Formula XII is 2-methylene-octanal, the compound of Formula XIII is 2-methylene-decanal; the compound of Formula XIV is 2-methylene-undecanal; the compound of Formula XV is 3-(4-methyl-cyclohex-3-enyl)-2-methylene-butyraldehyde; the compound of Formula XVI is 3,5,5-trimethyl-2-methylene-hexanal, which is also known under the trade name Alpha-Methylene Vandor B; the compound of Formula XVII is 3,7-dimethyl-2-methylene-oct-6-enal, which is also known under the trade name Bergamal and the compound of Formula XVIII is 2-(2,2,3-trimethyl-cyclopent-3-enyl)-acetaldehyde, which is also known under the trade name Alpha-Methylene Campholenic aldehyde.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as HPLC, and particularly gel chromatography and solid phase microextraction ("SPME").

We have discovered that the compounds of Formulae V-X have fresh, citrus, green violet, aldehydic musk, sweet, floral tones that are well suited for use as a fragrance ingredient.

Another embodiment of the invention is a method for enhancing a perfume by incorporating an olfactory acceptable amount of the compounds of structures below:

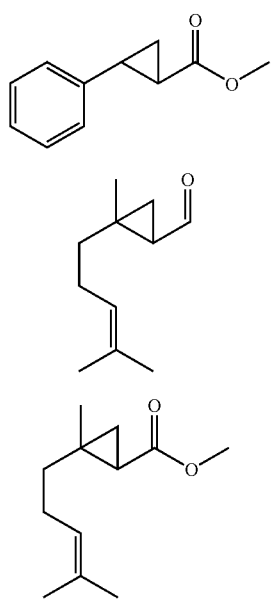

Formula II

Formula III

Formula IV

Compounds of Formulae II-IV may be prepared via Corey's cyclopropanation reaction from corresponding alkenes or dienes, similar to the preparation of compounds of Formulae V-XI, as described in the examples below.

Those with the skill in the art will appreciate that the compound of Formula II is 2-phenyl-cyclopropanecarboxylic acid methyl ester, the compound of Formula III is 2-methyl-2-(4-methyl-pent-3-enyl)-cyclopropanecarbaldehyde, the compound of Formula IV is 2-methyl-2-(4-methyl-pent-3-enyl)- cyclopropanecarboxylic acid methyl ester. The corresponding alkene of Formula II is 3-phenyl acrylic acid methyl ester; the corresponding alkene of Formula III is 3,7-dimethyl-octa-2,6-dienal, also known as Citral; the corresponding alkene of Formula IV is 3,7-dimethyl-octa-2,6-dienoic acid methyl ester.

We have discovered that the compounds of Formulae II-IV have fresh, citrus, cinnamon, aldehydic musk, sweet, floral tones that are well suited for use as fragrance ingredients.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc.

EXAMPLE A

Preparation of 1-hexyl-cyclopropanecarbaldehyde

To a dry 500 ml multi-neck round bottom flask fitted with an air stirrer, nitrogen inlet condenser and an addition funnel 4.4 g of 60% sodium hydride (NaH) and 150 ml of dimethyl sufoxide was added. The resulting mixture was heated to 50°

C. while being stirred. 24.6 g of trimethyloxosulphonioum iodide (($CH_3$)$_3$SOI) was added slowly. After the addition of ($CH_3$)$_3$SOI, 12.8 g of 2-methylene-octanal was added dropwise. The mixture was aged for 2 hours and a first sample was taken. The gas chromatography test indicated that 73.8% of the starting material converted into 1-hexyl-cyclopropanecarbaldehyde. The mixture was aged for another 90 minutes and a second sample was taken. The gas chromatography test indicated that 75% of the starting material converted into 1-hexyl-cyclopropanecarbaldehyde. The mixture was cooled and quenched with 250 ml of water. 100 ml of toluene was added and the mixture was stirred, allowed to settle and the organic layer separated.

The NMR spectrum of the 1-hexyl-cyclopropanecarbaldehyde is as follows: 0.7 ppm (s, 2H); 0.8 ppm (s, 5H); 0.9 ppm (s, 1H); 1.1 ppm (s, 1H); 1.2-1.3 ppm (m, 12H); 1.4 ppm (m, 2H); 1.5 ppm (m, 3H); 1.6-1.7 ppm (m, 3H); 1.8 ppm (m, 2H); 8.7 ppm (s, 1H).

EXAMPLE B

Preparation of 1-octyl-cyclopropanecarbaldehyde

To a dry 500 ml multi-neck round bottom flask fitted with an air stirrer, nitrogen inlet condenser and an addition funnel 4.4 g of 60% sodium hydride (NaH) and 150 ml of dimethyl sufoxide was added. The resulting mixture was heated to 50° C. while being stirred. 25 g of trimethyloxosulphonioum iodide (($CH_3$)$_3$SOI) was added slowly. After the addition of ($CH_3$)$_3$SOI, 15.6 g of 2-methylene-decanal was added dropwise. The mixture was aged for 2 hours and a first sample was taken. The gas chromatography test indicated that 73.8% of the starting material converted into 1-octyl-cyclopropanecarbaldehyde. The mixture was aged for another 90 minutes and a second sample was taken. The gas chromatography test indicated that 75% of the starting material converted into 1-octyl-cyclopropanecarbaldehyde. The mixture was cooled and quenched with 250 ml of water. 100 ml of toluene was added and the mixture was stirred, allowed to settle and the organic layer separated.

The NMR spectrum of the 1-octyl-cyclopropanecarbaldehyde is as follows: 0.8 ppm (s, 1H); 0.9 ppm (s, 3H); 1.0 ppm (s, 1H); 1.1 ppm (s, 1H); 1.2-1.3 ppm (m, 11H); 1.4 ppm (m, 1H); 1.5 ppm (m, 2H); 1.6 ppm (m, 2H); 1.7 ppm (d, 1H); 8.7 ppm (s, 1H).

EXAMPLE C

Preparation of 1-nonyl-cyclopropanecarbaldehyde

To a dry 500 ml multi-neck round bottom flask fitted with an air stirrer, nitrogen inlet condenser and an addition funnel 4.4 g of 60% sodium hydride (NaH) and 150 ml of dimethyl sufoxide was added. The resulting mixture was heated to 50° C. while being stirred. 24.8 g of trimethyloxosulphonioum iodide (($CH_3$)$_3$SOI) was added slowly. After the addition of ($CH_3$)$_3$SOI, 18.2 g of 2-mehylene-undecanal was added dropwise. The mixture was aged for 2 hours and a first sample was taken. The gas chromatography test indicated that 73.8% of the starting material converted into 1-nonyl-cyclopropanecarbaldehyde. The mixture was aged for another 90 minutes and a second sample was taken. The gas chromatography test indicated that 75% of the starting material converted into 1-nonyl-cyclopropanecarbaldehyde. The mixture was cooled and quenched with 250 ml of water. 100 ml of toluene was added and the mixture was stirred, allowed to settle and the organic layer separated.

The NMR spectrum of the 1-nonyl-cyclopropanecarbaldehyde is as follows: 0.8 ppm (s, 1H); 0.9 ppm (s, 3H); 1.0 ppm (s, 2H); 1.1 ppm (s, 2H); 1.3-1.5 ppm (m, 12H); 1.6 ppm (s, 3H); 1.8 ppm (s, 8H); 8.7 ppm (s, 1H).

EXAMPLE D

Preparation of 1-(1,3,3-trimethylbutyl)-cyclopropanecarboxaldehyde

To a dry 500 ml multi-neck round bottom flask fitted with an air stirrer, nitrogen inlet condenser and an addition funnel 4.4 g of 60% sodium hydride (NaH) and 150 ml of dimethyl sufoxide was added. The resulting mixture was heated to 50° C. while being stirred. 25 g of trimethyloxosulphonioum iodide (($CH_3$)$_3$SOI) was added slowly. After the addition of ($CH_3$)$_3$SOI, 15.4 g of 3,5,5-trimethyl-2-methylene-hexanal was added dropwise. The mixture was aged for 2 hours and a first sample was taken. The gas chromatography test indicated that 73.8% of the starting material converted into 1-(1, 3,3-trimethylbutyl)-cyclopropanecarboxaldehyde. The mixture was aged for another 90 minutes and a second sample was taken. The gas chromatography test indicated that 75% of the starting material converted into 1-(1,3,3-trimethylbutyl)-cyclopropanecarboxaldehyde. The mixture was cooled and quenched with 250 ml of water. 100 ml of toluene was added and the mixture was stirred, allowed to settle and the organic layer separated.

The NMR spectrum of the 1-(1,3,3-trimethylbutyl)-cyclopropanecarboxaldehyde is as follows: 0.7 ppm (s, 1H); 0.9 ppm (s, 16H); 1.0 ppm (s, 1H); 1.2 ppm (m, 7H); 1.3 ppm (s, 3H); 1.4-1.6 ppm (m, 7H); 8.9 ppm (s, 1H).

EXAMPLE E

Preparation of 1-(1,5-dimethyl-4-hexenyl)-cyclopropanecarboxaldehyde

To a dry 500 ml multi-neck round bottom flask fitted with an air stirrer, nitrogen inlet condenser and an addition funnel 2.2 g of 60% sodium hydride (NaH) was added and rinsed 3 times with 50 ml of hexane. Traces of hexane were removed under reduced pressure. 12.4 g of trimethyloxosulphonioum iodide (($CH_3$)$_3$SOI) was added slowly, followed by 10 ml and 65 ml portions of dimethyl sufoxide (DMSO). The resulting mixture was stirred for 30 minutes. 10 g of 3,7-dimethyl-2-methylene-oct-6-enal was added dropwise. After the mixture was aged overnight, samples were taken every two hours. The crude was quenched with 500 ml of cold water and the organic layer was extracted with diethyl ether. The extracts were washed with cold water and dried over anhydrous $MgSO_4$. The gas chromatography test indicated that 72% of the starting material converted into 1-(1,5-dimethyl-4-hexenyl)-cyclopropanecarboxaldehyde.

The NMR spectrum of the 1-(1,5-dimethyl-4-hexenyl)-cyclopropanecarboxaldehyde is as follows: 0.8-0.9 ppm (d, 2H); 1.0 ppm (s, 3H); 1.1 ppm (s, 2H); 1.4 ppm (m, 2H); 1.5 ppm (s, 4H); 1.6 ppm (s, 4H); 1.7 ppm (s, 3H); 2.0 ppm (s, 1H); 2.1 ppm (s, 1H); 5.1 ppm (s, 1H); 8.9 ppm (s, 1H).

EXAMPLE F

Preparation of 1-(2,2,3-trimethyl-3-cyclopenten-1-yl)-cyclopropanecarboxaldehyde To a dry 500 ml multi-neck round bottom flask fitted with an air stirrer, nitrogen inlet condenser and an addition funnel 4.2 g of 60% sodium hydride (NaH) was added and rinsed 3 times with 50 ml of hexane. Traces of hexane were removed under reduced pressure. 23.4 g of trimethyloxosulphonioum iodide (($CH_3$)$_3$SOI) was added slowly, followed by 100 ml of dimethyl sufoxide (DMSO). The resulting mixture was stirred for 30 minutes. 18 g of 2-(2,2,3-trimethyl-cyclopent-3-enyl)-acetaldehyde was added dropwise. After the mixture was aged overnight, samples were taken every two hours. The crude was quenched with 500 ml of cold water and the organic layer was extracted with diethyl ether. The extracts were washed with cold water and dried over anhydrous $MgSO_4$. The gas chromatography test indicated that 89% of the starting material converted into 1-(2,2,3-trimethyl-3-cyclopenten-1-yl)-cyclopropanecarboxaldehyde.

The NMR spectrum of the 1-(2,2,3-trimethyl-3-cyclopenten-1-yl)-cyclopropanecarboxaldehyde is as follows: 0.8 ppm (s, 3H); 0.9 ppm (s, 3H); 1.0 ppm (s, 1H); 1.1 ppm (s, 1H); 1.1 ppm (s, 5H); 1.2 ppm (s, 2H); 1.2 ppm (s, 1H); 1.2 ppm (s, 1H); 1.3 ppm (s, 1H); 1.3 ppm (s, 1H); 1.4-1.6 (m, 4H); 1.7 ppm (m, 1H); 1.8-2.0 ppm (m, 2H); 2.1 ppm (m, 1H); 2.2 ppm (m, 1H); 2.3 ppm (m, 1H); 3.3 ppm (m, 1H); 5.3 ppm (m, 1H); 9.2 ppm (s, 1H); 9.5 ppm (s, 1H).

EXAMPLE G

Preparation of 1-[1-(4-methyl-3-cyclohexen-1-yl)-ethyl]-cyclopropanecarboxaldehyde To a dry 500 ml multi-neck round bottom flask fitted with an air stirrer, nitrogen inlet condenser and an addition funnel 5 g of 60% sodium hydride (NaH) and 100 ml of dimethyl sufoxide (DMSO) along with 20 ml of tetrahydrofuran (THF) was added and stirred. 25 g of trimethyloxosulphonioum iodide (($CH_3$)$_3$SOI) was added slowly. The mixture was allowed to stand until gassing stopped. 19.8 g of 3-(4-methyl-cyclohex-3-enyl)-2-methylene-butyraldehyde was added dropwise. The crude was quenched with 500 ml of cold water and the organic layer was extracted with diethyl ether. The gas chromatography test indicated that 91.9% of the starting material converted into 1-[1-(4-methyl-3-cyclohexen-1-yl)-ethyl]-cyclopropanecarboxaldehyde.

The NMR spectrum of the 1-[1-(4-methyl-3-cyclohexen-1-yl)-ethyl]-cyclopropanecarboxaldehyde is as follows: 0.8 ppm (s, 2H); 1.0 ppm (s, 2H); 1.1 ppm (m, 4H); 1.2-1.4 ppm (m, 5H); 1.5 ppm (s, 2H); 1.7 ppm (s, 5H); 1.8 ppm (s, 2H); 1.9-2.1 ppm (s, 6H); 2.2 ppm (s, 2H); 5.3 ppm (d, 1H); 9.0 ppm (d, 1H).

EXAMPLE H

Preparation of 2-methyl-2-(4-methyl-pent-3-enyl)-cyclopropanecarboxylic acid methyl ester To a dry 2 L multi-neck round bottom flask fitted with an air stirrer, nitrogen inlet condenser and an addition funnel 46 g of 60% sodium hydride (NaH) and 600 g of dimethyl sufoxide (DMSO) was added. 270.7 g of trimethyloxosulphonioum iodide (($CH_3$)$_3$SOI) was added slowly, while maintaining the temperature of the mixture at 25° C. The mixture was aged for 2 hours. After aging 182.13 g of 3,7-dimethyl-octa-2,6-dienoic acid methyl ester was added dropwise, while maintaining the temperature of the mixture at 25° C. The mixture was aged for 1 hour at room temperature. After aging the mixture was heated to 50° C. and aged overnight. The crude was quenched with 500 ml of cold water and the organic layer was extracted with diethyl ether. The extracts were washed with cold water and dried over anhydrous $MgSO_4$. The gas chromatography test indicated that 80.3% of the starting material converted into 2-methyl-2-(4-methyl-pent-3-enyl)-cyclopropanecarboxylic acid methyl ester.

The NMR of -methyl-2-(4-methyl-pent-3-enyl)-cyclopropanecarboxylic acid methyl ester is as follows: 0.9 ppm (m, 1H); 1.0 ppm (m, 1H); 1.1 ppm (s, 1H); 1.2 ppm (s, 2H); 1.3 ppm (m, 1H); 1.4 ppm (m, 1H); 1.5 ppm (m, 1H); 1.6 ppm (s, 3H); 1.7 ppm (s, 3H); 2.1 ppm (m, 2H); 2.2 ppm (s, 1H); 3.7 ppm (d, 3H); 5.1 ppm (s, 1H);

EXAMPLE I

Incorporation of 1-(1,5-dimethyl-4-hexenyl)-cyclopropanecarboxaldehyde-Cyclopropanated Bergamal into a fragrance formulation

| | |
|---|---|
| Bergamot Oil | 45 |
| Citronella Oil Ceylon | 110 |
| Citronellyl Nitrile | 30 |
| Cyclopropanated Bergamal | 100 |
| Decyl Acetate | 7 |
| Diphenyl Oxide | 100 |
| Galaxolide | 130 |
| Hedione | 40 |
| Iso E Super | 60 |
| Lemon Oil | 40 |
| Methyl Benzoate | 2 |
| Methyl Beta Naph Ketone | 35 |
| Methyl Nonyl Acetald | 5 |
| Methyl Para Cresol | 6 |
| Phenyl Ethyl Acetate | 15 |
| Phenyl Ethyl Alcohol | 90 |
| Rose Oxide | 5 |
| Terpineol | 80 |
| Terpinolene | 100 |
| Total weight | 1000 |

EXAMPLE J

Incorporation of 2-methyl-2-(4-methyl-pent-3-enyl)-cyclopropanecarbaldehye-Cyclopropanated Citral into a fragrance formulation

| | |
|---|---|
| Carvone | 5 |
| Cyclopropanated Citral | 35 |
| Farnesene | 200 |
| Farnesol | 20 |
| Galaxolide | 125 |
| Geraniol | 10 |
| Geranyl Acetate | 20 |
| Geranyl Formate | 20 |
| Hedione | 65 |
| Helional | 100 |
| Hexenol, Cis 3 | 1 |
| Iso E Super | 100 |
| Jasmone Cis | 15 |
| Linalool | 90 |
| Methyl Geraniate | 38 |
| Nerolidol | 50 |
| Rose Oxide | 1 |
| Terpineol | 100 |
| Trimofix O | 5 |
| Total weight | 1000 |

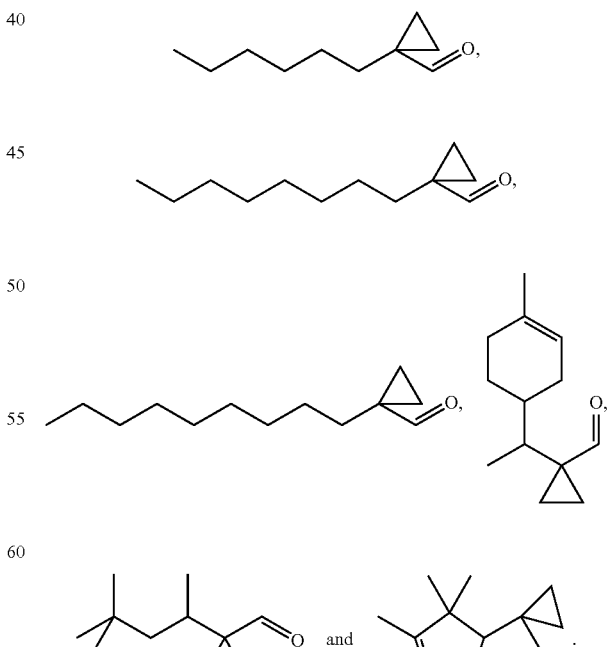

17. The fragrance product of claim 9, wherein the compound is selected from the group consisting of:
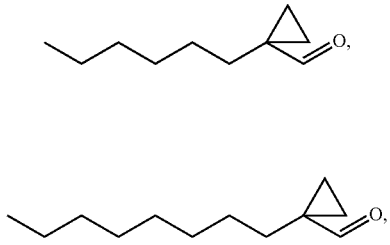
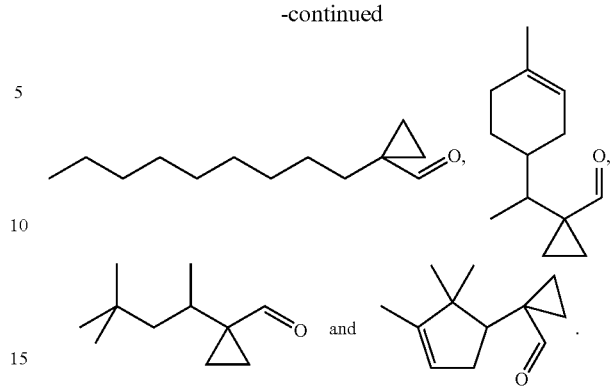

What is claimed is:

1. A method of improving, enhancing or modifying a fragrance formulation through the addition of an olfactory acceptable amount of a compound of formula:

wherein R is a straight, branched, or cyclic hydrocarbon moiety consisting of 6 to 15 carbon atoms and containing single and/or double bonds.

2. The method of claim 1, wherein the compound is selected from the group consisting of:

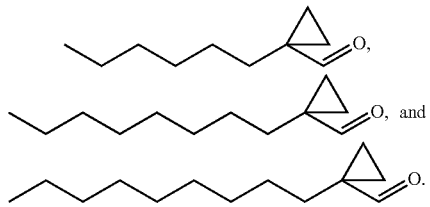

3. The method of claim 1, wherein the fragrance formulation is incorporated into a product selected from the group consisting of perfumes, colognes, toilet waters, cosmetic products, personal care products, fabric care products, cleaning products and air fresheners.

4. The method of claim 1, wherein the cleaning products are selected from the group consisting of detergents, dishwashing compositions, scrubbing compounds and window cleaners.

5. The method of claim 1, wherein the olfactory acceptable amount is from about 0.005 to about 10 weight percent.

6. The method of claim 1, wherein the olfactory acceptable amount is from about 0.5 to about 8 weight percent.

7. The method of claim 1, wherein the olfactory acceptable amount is from about 1 to about 7 weight percent.

8. A fragrance formulation containing an olfactory effective amount of a compound of formula:

wherein R is a straight, branched, or cyclic hydrocarbon moiety consisting of 6 to 15 carbon atoms and containing single and/or double bonds.

9. A fragrance product containing a compound of formula:

wherein R is a straight, branched, or cyclic hydrocarbon moiety consisting of 6 to 15 carbon atoms and containing single and/or double bonds.

10. The method of claim 1, wherein the compound is selected from the group consisting of:

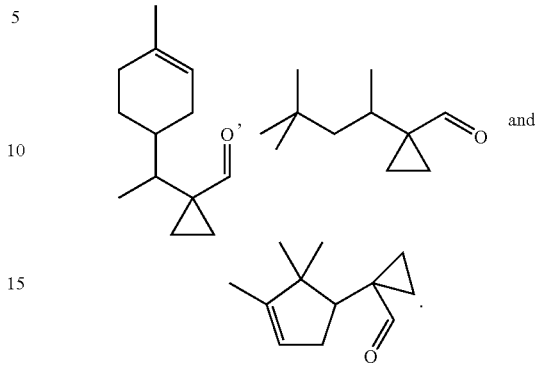

11. The method of claim 10, wherein the fragrance formulation is incorporated into a product selected from the group consisting of perfumes, colognes, toilet waters, cosmetic products, personal care products, fabric care products, cleaning products and air fresheners.

12. The method of claim 11, wherein the cleaning products are selected from the group consisting of detergents, dishwashing compositions, scrubbing compounds and window cleaners.

13. The method of claim 10, wherein the olfactory acceptable amount is from about 0.005 to about 10 weight percent.

14. The method of claim 10, wherein the olfactory acceptable amount is from about 0.5 to about 8 weight percent.

15. The method of claim 10, wherein the olfactory acceptable amount is from about 1 to about 7 weight percent.

16. The fragrance formulation of claim 8, wherein the compound is selected from the group consisting of: